United States Patent [19]

Hurnaus et al.

[11] Patent Number: 5,232,946
[45] Date of Patent: Aug. 3, 1993

[54] PHENYLETHANOLAMINES, THEIR USE AS PHARMACEUTICALS AND AS PERFORMANCE ENHANCERS IN ANIMALS

[75] Inventors: Rudolf Hurnaus; Manfred Reiffen, both of Biberach; Robert Sauter, Laupheim; Wolfgang Grell, Biberach; Eckhard Rupprecht, Aulendorf-Tannhausen, all of Fed. Rep. of Germany

[73] Assignee: Dr. Karl Thomae GmbH, D-7950 Biberach an der Riss, Fed. Rep. of Germany

[21] Appl. No.: 572,969

[22] PCT Filed: Nov. 29, 1988

[86] PCT No.: PCT/EP88/01083
§ 371 Date: Aug. 20, 1990
§ 102(e) Date: Aug. 20, 1990

[87] PCT Pub. No.: WO90/06299
PCT Pub. Date: Jun. 14, 1990

[51] Int. Cl.⁵ .................. A61K 31/22; A61K 31/265; A61K 31/275; A61K 31/195
[52] U.S. Cl. .................. 514/546; 514/512; 514/522; 514/564; 514/567; 514/622; 514/651; 514/652; 514/653
[58] Field of Search .......... 514/651, 652, 653

[56] References Cited

PUBLICATIONS

Chemical Abstracts (108: 111962h) 1987.

Primary Examiner—Frederick E. Waddell
Assistant Examiner—K. Weddington
Attorney, Agent, or Firm—David E. Frankhouser; Alan R. Stempel; Mary-Ellen M. Timbers

[57] ABSTRACT

The invention relates to new phenylethanolamines of general formula

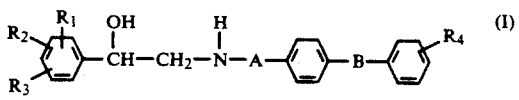

wherein
A represents a straight-chained or branched alkylene group,
B represents a bond, an alkylene group, a carbonyl or hydroxymethylene group,
$R_1$ represents a hydrogen atom, a halogen atom or a trifluoromethyl group,
$R_2$ represents a hydrogen atom or an amino group,
$R_3$ represents a cyano group, a hydrogen, chlorine or bromine atom and
$R_4$ represents a hydrogen or halogen atom, an alkyl, hydroxy, alkoxy, carboxy, alkoxycarbonyl, aminocarbonyl, alkylaminocarbonyl or dialkylaminocarbonyl group or an alkoxy group substituted in the end position by a carboxy, alkoxycarbonyl, aminocarbonyl, alkylaminocarbonyl, dialkylaminocarbonyl, hydroxy, alkoxy, amino, alkylamino, dialkylamino, pyrrolidino, piperidino or hexamethyleneimino group, the optical isomers and diastereoisomers and acid addition salts thereof.

The new compounds of formula I, the optical isomers and diastereoisomers and acid addition salts thereof, particularly the physiologically acceptable acid addition salts thereof with inorganic or organic acids, have valuable pharmacological properties, namely an effect on the metabolism, preferably the effect of lowering blood sugar and reducing body fat and they may also be used as performance enhancers in animals.

The new compounds of general formula I above may be prepared by methods known per se.

5 Claims, No Drawings

PHENYLETHANOLAMINES, THEIR USE AS PHARMACEUTICALS AND AS PERFORMANCE ENHANCERS IN ANIMALS

This invention relates to new phenylethanolamines of formula

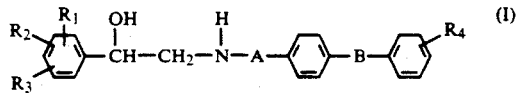

the optical isomers, diastereoisomers and acid addition salts thereof, particularly for pharmaceutical use the physiologically acceptable acid addition salts, which have valuable pharmacological properties, namely an effect on the metabolism, particularly the effect of lowering blood sugar, reducing body fat and increasing energy consumption, and lowering the atherogenic lipoproteins VLDL and LDL.

The new compounds may also be used as performance enhancers in animals, particularly in order to achieve higher daily weight increases and improved food utilisation in animal feeding, preferably in the fattening of animals, which is a further object of the invention.

In general formula I above

A represents a straight-chained or branched alkylene group with 1 to 5 carbon atoms, B represents a bond, an alkylene group with 1 or 2 carbon atoms, a carbonyl or hydroxymethylene group, $R_1$ represents a hydrogen atom, a halogen atom or a trifluoromethyl group, $R_2$ represents hydrogen atom or an amino group, $R_3$ represents a cyano group, a hydrogen, chlorine or bromine atom and $R_4$ represents a hydrogen or halogen atom, an alkyl, hydroxy, alkoxy, carboxy, alkoxycarbonyl, aminocarbonyl, alkylaminocarbonyl or dialkylaminocarbonyl group, an alkoxy group with 1 to 3 carbon atoms substituted in the end position by a carboxy, alkoxycarbonyl, aminocarbonyl, alkylaminocarbonyl or dialkylaminocarbonyl group, or an alkoxy group with 2 or 3 carbon atoms substituted in the end position by a hydroxy, alkoxy, amino, alkylamino, dialkylamino, pyrrolidino, piperidino or hexamethyleneimino group, whilst all the above-mentioned alkyl or alkoxy groups may contain from 1 to 3 carbon atoms, unless otherwise stated.

As examples of the definitions of the groups given hereinbefore:

A may represent a methylene, 1-ethylidene, 1-n-propylidene, 1-n-butylidene, ethylene, 1-methylethylene, 2-methyl-ethylene, 1-ethyl-ethylene, 2-ethyl-ethylene, 1,2-dimethyl-ethylene, 1,1-dimethylethylene, 1-ethyl-1-methylethylene, 2,2-dimethyl-ethylene, 2-ethyl-2-methyl-ethylene, n-propylene, 1-methyl-n-propylene, 2-methyl-n-propylene, 3-methyl-n-propylene, 1-ethyl-n-propylene, 2-ethyl-n-propylene, 3-ethyl-n-propylene, 1,1-dimethyl-n-propylene, 2,3-dimethyl-n-propylene, 3,3-dimethyl-n-propylene, n-butylene or n-pentylene group, B represents a bond, a methylene, ethylene, 1-ethylidene, carbonyl or hydroxymethylene group, $R_1$ represents a hydrogen, fluorine, chlorine or bromine atom or a trifluoromethyl group, $R_2$ represents a hydrogen atom or an amino group, $R_3$ represents a hydrogen, chlorine or bromine atom or a cyano group and $R_4$ represents a hydrogen, fluorine, chlorine or bromine atom, a methyl, ethyl, n-propyl, isopropyl, hydroxy, methoxy, ethoxy, n-propoxy, isopropoxy, n-butoxy, carboxy, methoxycarbonyl, ethoxycarbonyl, n-propoxycarbonyl, aminocarbonyl, methylaminocarbonyl, ethylaminocarbonyl, isopropylaminocarbonyl, dimethylaminocarbonyl, diethylaminocarbonyl, di-n-propylaminocarbonyl, N-ethyl-methylaminocarbonyl, N-ethyl-isopropylaminocarbonyl, 2-hydroxy-ethoxy, 3-hydroxy-n-propoxy, 2-methoxy-ethoxy, 2-ethoxy-ethoxy, 2-n-propoxyethoxy, 3-ethoxy-n-propoxy, 2-amino-ethoxy, 2-methylamino-ethoxy, 2-dimethylamino-ethoxy, 2-isopropylaminoethoxy, 2-di-n-propylamino-ethoxy, 2-(1-pyrrolidino)-ethoxy, 2-(1-piperidino)ethoxy, 2-(1-hexamethyleneimino)-ethoxy, 3-amino-n-propoxy, 3-diethylamino-n-propoxy, 3-(1-piperidino)-n-propoxy, carboxymethoxy, 2-carboxyethoxy, 3-carboxy-n-propoxy, methoxycarbonylmethoxy, 2-methoxycarbonyl-ethoxy, ethoxycarbonylmethoxy, 2-ethoxycarbonyl-ethoxy, 3-ethoxycarbonyl-n-propoxy, n-propoxycarbonylmethoxy, 2-isopropoxycarbonyl-ethoxy, aminocarbonylmethoxy, 2-aminocarbonyl-ethoxy, ethoxy, dimethylaminocarbonylmethoxy, 2-dimethylamino-carbonyl-ethoxy, diethylaminocarbonylmethoxy, 2-diethylaminocarbonylethoxy, or 2-di-n-propylaminocarbonyl-ethoxy group.

By way of example, in addition to the compounds mentioned in the Examples, mention should also be made of the following compounds which are covered by general formula I given hereinbefore:

ethyl 4'-[2-[N-(2-(4-amino-3-cyano-5 fluoro-phenyl)-2-hydroxy-ethyl)-amino]propyl]diphenylmethane-2-carboxylate, ethyl 4'-[2-[N-(2-(4-amino-3-cyano-5-fluoro-phenyl)-2-hydroxy-ethyl)-amino]propyl]biphenylyl-4-carboxylate, ethyl 4'-[2-[N-(2-(4-amino-3-cyano-5-fluoro-phenyl)-2-hydroxy-ethyl)-amino]propyl]biphenylyl-4-oxyacetate ethyl 4'-[2-[N-(2-(4-amino-3-cyano-5-fluoro-phenyl)-2-hydroxy-ethyl)-amino]propyl]biphenylyl-2-carboxylate, 4'-[2-[N-(2-(3-chloro-phenyl)-2-hydroxy-ethyl)amino]-propyl]-biphenylyl-4-oxyacetic acid amide and 4'-[2-[N-(2-(3-chloro-phenyl)-2-hydroxy-ethyl)amino]-propyl]-[2-(2-ethoxy)ethoxy]biphenyl, the optical isomers, diastereoisomers and addition salts thereof, more particularly the physiologically acceptable addition salts thereof.

However, preferred compounds of formula I are those wherein

A represents an ethylene group optionally substituted by an alkyl group with 1 to 3 carbon atoms or by two methyl groups, B represents a bond, a methylene, ethylene, hydroxymethylene or carbonyl group, $R_1$ represents a hydrogen, fluorine, chlorine or bromine atom or a trifluoromethyl group, $R_2$ represents a hydrogen atom or an amino group, $R_3$ represents a hydrogen atom, a chlorine atom or a cyano group and $R_4$ represents a hydrogen atom, a chlorine atom, a hydroxy, methoxy, methyl, ethyl, carboxy, methoxycarbonyl, ethoxycarbonyl, carboxymethoxy, 2-hydroxyethoxy, methoxycarbonylmethoxy or ethoxycarbonylmethoxy group, the optical isomers, diastereoisomers and addition salts thereof, particularly the physiologically acceptable addition salts thereof.

However, particularly preferred compounds of the present invention are the compounds of general formula

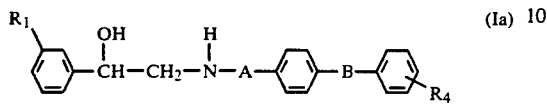
(Ia)

wherein

A represents an ethylene or methylethylene group,

B represents a bond or a methylene group, $R_1$ represents a hydrogen or chlorine atom and $R_4$ represents a hydrogen atom, a methyl, ethyl, hydroxy, methoxy, methoxycarbonyl, ethoxycarbonyl, 2-hydroxy-ethoxy, methoxycarbonylmethoxy or ethoxycarbonylmethoxy group in the 2 or 4 position, the optical isomers, diastereoisomers and addition salts thereof, particularly the physiologically acceptable addition salts thereof.

According to the invention the new compounds are obtained by the following processes:

a) reacting a compound of general formula

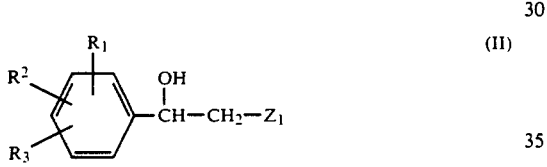
(II)

with a compound of general formula

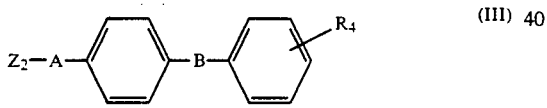
(III)

wherein

A, B and $R_1$ and to $R_4$ are as hereinbefore defined, one of the groups $Z_1$ or $Z_2$ represents a nucleophilic leaving group and the other group $Z_1$ or $Z_2$ represents an amino group.

Examples of nucleophilic leaving groups include halogen atoms or sulphonyloxy groups, e.g. a chlorine, bromine or iodine atom, a methanesulphonyloxy, p-toluenesulphonyloxy or ethoxysulphonyloxy group.

The reaction is conveniently carried out in a solvent or mixture of solvents such as acetone, diethylether, acetonitrile, dimethylformamide, dimethylsulphoxide, methylene chloride, chloroform, tetrahydrofuran, dioxan or an excess of the compounds of general formulae II and/or III used and optionally in the presence of an acid-binding agent, e.g. an alkoxide such as potassium tert.butoxide, an alkali metal hydroxide such as sodium or potassium hydroxide, an alkali metal carbonate such as potassium carbonate, a tertiary organic base such as triethylamine, N,N-diisopropylethylamine or pyridine, whilst the latter may simultaneously also serve as solvent, or a reaction accelerator such as potassium iodide, depending on the reactivity of the nucleophilically exchangeable group, conveniently at temperatures of between 0° and 150° C., preferably at temperatures of between 20° and 100° C., e.g. at the boiling temperature of the solvent used. The reaction may, however, also be carried out without a solvent. It is particularly advantageous, however, to perform the reaction in the presence of a tertiary organic base or an excess of the amine of general formula II or III used.

b) Reduction of a Schiff base of general formula

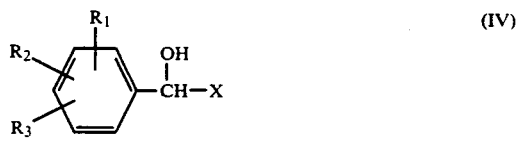
(IV)

optionally formed in the reaction mixture, wherein $R_1$ to $R_3$ are as hereinbefore defined and X represents a group of formula

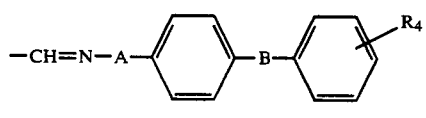

or

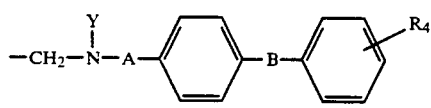

wherein

A, B and $R_4$ are as hereinbefore defined and Y together with a hydrogen atom of the adjacent carbon atom of group A represents another bond.

The reduction is carried out in a suitable solvent such as methanol, ethanol, diethylether, tetrahydrofuran, dioxan, ethyl acetate or ethanol/ethyl acetate with hydrogen in the presence of a hydrogenation catalyst such as platinum, palladium/charcoal or Raney nickel under a hydrogen pressure of 1 to 5 bar or with a metal hydride such as lithium aluminium hydride, diborane, sodium cyanoborohydride or borane/dimethylsulphide, but preferably with sodium borohydride or sodium cyanoborohydride at temperatures of between 0° and 50° C., preferably at ambient temperature. In the reduction with a complex metal hydride such as lithium aluminium hydride, diborane or borane/dimethylsulphide, any carbonyl or nitrile function present may also be reduced.

c) Reduction of a compound of general formula

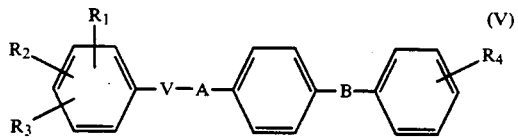
(V)

optionally formed in the reaction mixture wherein A, B and $R_1$ to $R_4$ are as hereinbefore defined and V represents a group of formula

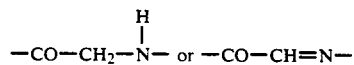

The reduction is preferably carried out in a suitable solvent such as methanol, ethanol, diethylether or tetrahydrofuran in the presence of a metal hydride such as sodium borohydride, lithium aluminium hydride, diborane, borane/dimethylsulphide or sodium cyanoborohydride, but preferably with sodium borohydride in methanol or ethanol, at between 0° and 40° C., but preferably at ambient temperature.

In the reduction with a complex metal hydride such as sodium borohydride, lithium aluminium hydride, diborane or borane/dimethylsulphide, any carbonyl or nitrile function present may also be reduced.

d) Reaction of a compound of general formula

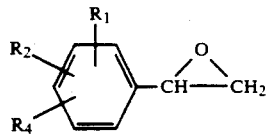

wherein $R_1$ to $R_3$ are as hereinbefore defined, with an amine of general formula

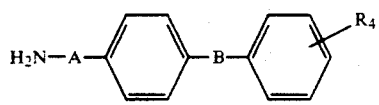

wherein

A, B and $R_4$ are defined as hereinbefore.

The reaction is preferably carried out in a solvent such as ethanol, isopropanol, tetrahydrofuran, dioxan, dimethylformamide, dimethylsulphoxide or acetonitrile/ethanol, conveniently at temperatures of between 50° and 100° C. However, the reaction may also be carried out without a solvent.

e) Reduction of a compound of general formula

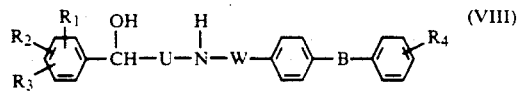

optionally formed in the reaction mixture wherein B and $R_1$ to $R_4$ are as hereinbefore defined, U represents a carbonyl group and W has the meanings given for A hereinbefore or U represents a methylene group and W represents an alkanone group with 1 to 5 carbon atoms, whilst the carbonyl group must be linked to the nitrogen atom of the NH group.

The reduction is carried out in a suitable solvent such as diethylether or tetrahydrofuran with a reducing agent such as a metal hydride, e.g. with lithium aluminium hydride, diborane or diborane/dimethylsulphide, but preferably with sodium borohydride in the presence of glacial acetic acid or trifluoroacetic acid, at temperatures of between 0° and 100° C., preferably at temperatures of between 10° and 50° C. In the reduction any carbonyl or nitrile function present is simultaneously also reduced.

f) In order to prepare compounds of general formula I wherein $R_3$ is a hydrogen, chlorine or bromine atom and $R_4$ is an alkoxy group with 2 or 3 carbon atoms substituted in the end position by a hydroxy, alkoxy, amino, alkylamino, dialkylamino, pyrrolidino, piperidino or hexamethyleneimino group: reduction of a compound of general formula

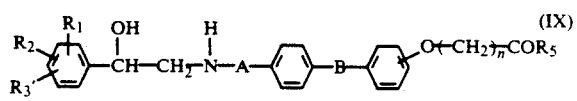

wherein

A, B, $R_1$ and $R_2$ are as hereinbefore defined $R_3'$ represents a hydrogen, chlorine or bromine atom, n represents the number 1 or 2 and $R_5$ represents a hydroxy, alkoxy, amino, alkylamino, dialkylamino, pyrrolidino, piperidino or hexamethyleneimino group.

The reduction is carried out in a suitable solvent such as diethylether or tetrahydrofuran with a reducing agent such as a metal hydride, e.g. with lithium aluminium hydride, diborane, diborane/dimethylsulphide or with sodium borohydride in the presence of glacial acetic acid or trifluoroacetic acid, at temperatures of between 0° and 100° C., but preferably at temperatures of between 10° and 50° C. In the reaction a carbonyl group contained in the moiety B may simultaneously also be reduced.

g) In order to prepare compounds of general formula I wherein $R_4$ represents an alkoxycarbonyl, aminocarbonyl, alkylaminocarbonyl or dialkylaminocarbonyl group, an alkoxy group with 1 to 3 carbon atoms substituted in the end position by an alkoxycarbonyl, aminocarbonyl, alkylaminocarbonyl or dialkylaminocarbonyl group:

reaction of a compound of general formula

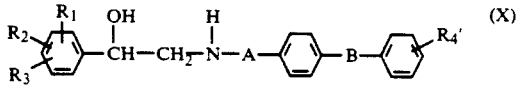

wherein

A, B and $R_1$ to $R_3$ are as hereinbefore defined and $R_4'$ represents a carboxy group or an alkoxy group with 1 to 3 carbon atoms substituted in the end position by a carboxy group, or the reactive derivatives thereof such as the activated esters thereof, with a compound of general formula

wherein $R_6$ represents an alkoxy, amino, alkylamino, dialkylamino, pyrrolidino, piperidino or hexamethyleneimino group, whilst the alkyl or alkoxy moiety may contain from 1 to 3 carbon atoms.

The esterification or amidation is conveniently carried out in a solvent such as methylene chloride, chloroform, ether, tetrahydrofuran, dioxan, toluene or dimethylformamide, but particularly advantageously in an excess of a compound of general formula XI used, e.g. in methanol, ethanol, n-propanol, isopropanol, ammonia, methylamine, ethylamine, dimethylamine, diethylamine or piperidine, optionally in the presence of an acid-activating agent or a dehydrating agent, e.g. in the presence of ethyl chloroformate, thionylchloride, phosphorus trichloride, phosphorus pentoxide, N,N'-dicyclohexylcarbodiimide, N,N'-dicyclohexylcarbodiimide/N-hydroxy-succinimide, N,N'-carbonyldiimidazole or N,N'-thionyldiimidazole or triphenylphosphine/carbon tetrachloride, or an agent which activates the amino group, e.g. phosphorus trichloride, and optionally in the presence of an inorganic base such as sodium carbonate or a tertiary organic base such as triethylamine or pyridine, which may simultaneously serve as solvent, at temperatures of between $-25°$ C. and 150° C., but preferably at temperatures of between $-10°$ C. and the boiling temperature of the solvent used.

In the processes described hereinbefore, any reactive groups present such as imino, amino, alkylamino, hydroxy and/or carboxy groups may be protected during the reaction if necessary. Suitable protecting groups for imino, amino or alkylamino groups include acetyl, benzoyl, tert.butoxycarbonyl, benzyloxycarbonyl, benzyl, trityl or fluorenylmethyloxycarbonyl groups, for hydroxy groups acetyl, benzoyl, benzyl, trimethylsilyl or trityl groups and for carboxy groups benzyl or tert.butyl groups.

Any splitting off of a protecting group which may be necessary after the reaction is preferably carried out hydrolytically in an aqueous solvent, e.g. in water, isopropanol/water, tetrahydrofuran/water, dioxan/water or glacial acetic acid, in the presence of an acid such as hydrochloric, sulphuric or hydrobromic acid or in the presence of an alkali metal base such as sodium hydroxide or potassium hydroxide at temperatures of between 0° and 150° C., preferably at the boiling temperature of the reaction mixture. If a benzyl or benzyloxycarbonyl group is split off, however, this is preferably done hydrogenolytically, e.g. with hydrogen in the presence of a catalyst such as palladium/charcoal in a solvent such as methanol, ethanol, ethyl acetate or glacial acetic acid, optionally with the addition of an acid such as hydrochloric acid at temperatures of between 0° and 50° C., but preferably at ambient temperature, under a hydrogen pressure of 1 to 7 bar, preferably 3 to 5 bar.

If according to the invention a compound of general formula I is obtained wherein $R_4$ represents or contains an alkoxycarbonyl group or one of the above-mentioned amidocarbonyl groups, this may be converted by hydrolysis into a corresponding compound of general formula I wherein $R_4$ represents or contains a carboxy group or if a compound of general formula I is obtained wherein $R_4$ represents one of the above-mentioned alkoxy groups, this may be converted by ether cleavage into a corresponding compound of general formula I wherein $R_4$ represents a hydroxy group.

The subsequent hydrolysis is carried out either in the presence of an acid such as hydrochloric, sulphuric or trifluoroacetic acid or in the presence of a base such as sodium hydroxide or potassium hydroxide in a suitable solvent such as water, methanol, ethanol, ethanol/water, water/isopropanol or water/dioxan at temperatures of between $-10°$ C. and 120° C., e.g. at temperatures of between ambient temperature and the boiling temperature of the reaction mixture.

The subsequent ether cleavage is carried out in the presence of an acid such as hydrochloric, hydrobromic, sulphuric acid or boron tribromide in a suitable solvent such as methanol, ethanol, water/isopropanol, methylene chloride, chloroform or carbon tetrachloride at temperatures of between $-30°$ C. and the boiling temperature of the reaction mixture or, in the case of a benzylether, with hydrogen in the presence of a hydrogenation catalyst.

As already mentioned hereinbefore, the new compounds may occur in the form of their enantiomers or mixtures of enantiomers or, if they contain at least 2 asymmetric carbon atoms, they may also occur in the form of their diastereoisomers or mixtures of diastereoisomers.

Thus, the compounds of general formula I obtained which contain only one optically active centre may be separated into their optical antipodes by methods known per se (see Allinger N. L. and Eliel E. L. in "Topics in Stereochemistry", Vol. 6, Wiley Interscience, 1971), e.g. by recrystallisation from an optically active solvent or by reaction with an optically active substance which forms salts with the racemic compound, more particularly an acid, and separating the salt mixture thus obtained, e.g. on the basis of different solubilities, into the diastereoisomeric salts from which the free antipodes can be liberated by reaction with suitable agents. Particularly common optically active acids include, for example, the D and L forms of tartaric acid, di-O-benzoyltartaric acid, malic acid, mandelic acid, camphorsulphonic acid, glutaminic acid, aspartic acid or quinic acid.

Furthermore, the compounds of general formula I obtained which have at least 2 asymmetric carbon atoms may be separated into their diastereoisomers on the basis of their physical-chemical differences by methods known per se, e.g. by chromatography and/or fractional crystallisation. A pair of enantiomers thus obtained may then be separated into its optical antipodes as described above. If for example a compound of general formula I contains two optically active carbon atoms, the corresponding (R R', S S') and (R S', S R') forms are obtained.

Moreover, the compounds of general formula I obtained may be converted into the addition salts thereof, more particularly, for pharmaceutical use, the physiologically acceptable salts thereof with inorganic or organic acids. Examples of acids for this purpose include hydrochloric, hydrobromic, sulphuric, phosphoric, acetic, oxalic, malonic, fumaric, maleic, succinic, ascorbic, malic, tartaric, lactic, citric, benzoic, methanesulphonic, toluenesulphonic, phthalic, naphthalenesulphonic, nicotinic, palmitic or embonic acid.

The compounds of general formulae II to XI used as starting materials may be obtained by methods known from the literature or are known from the literature themselves.

Thus, for example, a starting compound of general formula II may be obtained by Friedel-Crafts acetylation of a corresponding compound, subsequent bromination and if necessary subsequent reaction with urotropine followed by hydrolysis. A ketone thus obtained is subsequently reduced.

A starting compound of general formula IV is obtained by reaction a corresponding carbonyl compound with a corresponding amine.

A starting compound of general formula V is obtained by reacting a corresponding haloacetyl or glyoxal compound with a corresponding amine.

A starting compound of general formula VIII is obtained by reacting a corresponding carboxylic acid with a corresponding amine in the presence of an acid-activating agent.

A starting compound of general formulae IX and X is obtained by reacting a suitable α-halo alcohol with a corresponding amine.

As already mentioned above, the new compounds of general formula I, the enantiomers or mixtures of enantiomers or, provided that they contain at least 2 asymmetric carbon atoms, the diastereoisomers or mixtures of diastereoisomers thereof and the acid addition salts thereof, particularly for pharmaceutical use the physiologically acceptable acid addition salts thereof, have valuable pharmacological properties, particularly an effect on the metabolism, preferably the effect of lowering blood sugar, reducing body fat and increasing energy consumption, as well as lowering the atherogenic lipoproteins VLDL and LDL.

For example, the following compounds were investigated for their biological properties as described below:

A = ethyl 4'-[2-[N-(2-(3-chloro-phenyl)-2-hydroxyethyl)amino]propyl]biphenylyl-4-carboxylate, B = methyl 4'-[2-[N-(2-hydroxy-2-phenyl-ethyl)amino]propyl]biphenylyl-4-oxyacetate, C = methyl 4'-[2-[N-(2-(3-chloro-phenyl)-2-hydroxyethyl)amino]propyl]biphenylyl-4-oxyacetate, D = 4'-2-[N-(2-(3-chloro-phenyl)-2-hydroxy-ethyl)amino]propyl]-4-(2-hydroxy-ethoxy)biphenyl, E = 4'-[2-[N-(2-(3-chloro-phenyl)-2-hydroxy ethyl)amino]propyl]-4-ethyl-biphenyl, F = 4'-[2-[N-(2-(3-chloro-phenyl)-2-hydroxy-ethyl)amino]ethyl]diphenylmethane, G = ethyl 4'-[2-[N-(2-(3-chloro-phenyl)-2-hydroxyethyl)amino]ethyl]diphenylmethane-2-carboxylate and H = ethyl 4'-[2-[N-(2-(3-chloro-phenyl)-2-hydroxyethyl)amino]propyl]diphenylmethane-2-carboxylate.

1. Antidiabetic Activity

The antidiabetic activity of the compounds according to the invention can be measured as a blood sugar-reducing effect in experimental animals. The substances to be tested were suspended in 1.5% methyl cellulose and administered by means of oesophageal tube to female mice reared by ourselves. 30 minutes later 1 g of glucose per kg of body weight dissolved in water was administered subcutaneously. Another 30 minutes later blood was taken from the retroorbital venosus plexus. From the serum, the glucose level was determined by the hexokinase method using an analytical photometer.

The Table which follows shows the lowering of blood sugar observed in this test as a percentage of a control group which was conducted simultaneously. Statistical evaluation was carried out by the students t-test taking $p = 0.05$ as the limit of significance.

| Compound | % Change from the control level Dosage [mg/kg] | |
|---|---|---|
| | 1 | 3 |
| A | −37 | −49 |
| B | −29 | −34 |
| C | −27 | −44 |
| D | | −62 |
| E | −29 | −40 |
| F | −21 | −39 |
| G | −35 | −50 |
| H | | −62 |

2. Antiadipose Activity

The antiadipose activity of the compounds according to the invention, which takes the form of an increase in lipolysis, was measured by means of the rise in glycerol in the serum. The test procedure is identical with that described above for testing for a blood sugar reducing effect. Glycerol was determined in a combined enzymatic-colorimetric test using an analytical photometer. The results are shown in the following Table as a percentage of a control group conducted simultaneously.

| Compound | % Change from the control level Dosage [mg/kg] | |
|---|---|---|
| | 1 | 3 |
| A | 121 | 220 |
| B | 194 | 301 |
| C | | 185 |
| D | | 378 |
| E | 141 | 165 |
| F | 80 | 182 |
| G | 143 | 364 |
| H | | 402 |

Furthermore, in the investigations of the substances according to the invention described above, at the dosages used, no circulatory effects could be observed nor were there any toxic side effects up to a dosage of 30 mg/kg. The substances are therefore well tolerated.

In view of their pharmacological properties, therefore, the new compounds of general formula I and the physiologically acceptable addition salts thereof with inorganic or organic acids are suitable for treating both diabetes mellitus and also obesity, thus in particular for the treatment of obese diabetics. The dosage required may be adapted to the metabolic physiological requirements of the individual patient, since the substances are free from any effects on the heart or circulation over a wide dosage range. In adults, therefore, the daily doses range from 1 to 300 mg, preferably 1 to 100 mg, distributed over 1 to 4 doses per day. For this purpose, the above-mentioned compounds, optionally in conjunction with other active substances, may be incorporated in the usual galenic preparations such as powders, tablets, coated tablets, capsules, suppositories or suspensions.

Furthermore, owing to their body fat-reducing (lipolytic) activity, the above-mentioned compounds may be used to treat obese animals and reduce or prevent undesirable fatty deposits in the fattening of animals and hence to improve the meat quality of fattened animals. Moreover, the above-mentioned compounds may be used to achieve higher daily weight increases and improved food utilisation in animal nutrition, preferably in the fattening of animals.

The performance-enhancing and fat-reducing activity of the above-mentioned compounds of formula I was tested, for example, on substances A, C and H as follows:

1.) 4 groups of 20 (control) and 10 (experimental groups A, C and H) male mice, each animal being kept on its own, were given identical food and water ad libitum. In addition, the experimental groups were given 20 ppm of the compounds mentioned above (A, C and H) in their food. The test period lasted 14 days.

The following Table shows the results found as relative changes compared with the control (control = 100):

| | A | C | H |
|---|---|---|---|
| Starting weight | 101.2 | 100.3 | 99.3 |
| Weight gain | 90.5 | 183.2 | 239.5 |

-continued

|  | A | C | H |
|---|---|---|---|
| Food uptake | 91.6 | 106.0 | 106.5 |
| Weight gain/food intake | 99.1 | 173.0 | 225.1 |

2.) 4 groups of 20 (control) and 10 (experimental groups A, C and H) male mice, each animal being kept separately, were given identical food and water ad libitum. The experimental groups were additionally given 10 mg/kg of body weight of the above-mentioned compounds p.o. The test period was 4 days.

The following Table contains the results found as relative changes compared with the control (control=100):

|  | A | C | H |
|---|---|---|---|
| Weight gain/food intake | 90.5 | 122.5 | 54.5 |
| Epididymal fatty deposits | 89.6 | 97.7 | 74.2 |
| Musculus gastrocnemius | 111.4 | 103.3 | 110.7 |
| Musculus soleus | 115.1 | 120.2 | 108.7 |
| Meat: fat ratio | 126.0 | 112.2 | 147.0 |

In view of these properties, the active substances mentioned above may be used as performance enhancers in animals in order to promote and accelerate growth, production of milk and wool and to improve feed utilisation, quality of the carcass and in order to shift the meat:fat ratio towards a higher meat content. The active substances can be used in farmed, cultivated and decorative animals and pets.

Farmed and cultivated animals include mammals such as cattle, e.g. calves, oxen, hulls, heifers and cows, buffalo, pigs, horses, sheep, goats, rabbits, hares, deer, animals farmed for their skins such as mink and chinchilla, birds such as doves, chickens, geese, ducks, turkeys, guinea-fowl, pheasants and quail, fish such as carp, trout, salmon, eels, tench and pike, or reptiles such as snakes and crocodiles.

Examples of decorative animals and pets include mammals such as dogs and cats, birds such as parrots, canaries, fish such as ornamental and aquarium fish, e.g. goldfish.

The active substances are used irrespective of the sex of the animal throughout all growth and performance phases of the animal. Preferably, the active substances are used during the intensive growth and performance phase. The intensive growth and performance phase lasts from one month to ten years depending on the type of animal.

The quantity of active substances administered to the animals in order to achieve the desired effect may be varied substantially on account of the favourable properties of the active substances. It is preferably around 0.001 to 50 mg/kg, more particularly 0.01 to 10 mg/kg of body weight per day. The appropriate quantity of active substance and the appropriate duration of administration depend particularly on the type of animal, its age, sex, state of health and the type of keeping and feeding of the animal and can easily be determined by anyone skilled in the art.

The active substances are administered to the animals by the usual methods. The type of administration depends in particular on the type of animal, its behaviour and its state of health.

The active substances may be administered once. However, they may also be administered temporarily or continuously throughout the entire growth phase or only part of it. If they are administered continuously, they may be given one or more times a day at regular or irregular intervals.

They are administered orally or parenterally in suitable formulations or in pure form. Oral formulations may be, for example, powders, tablets, granules, drenches, boli and feedstuffs, premixes for feedstuffs, formulations for adding to drinking water.

The oral formulations contain the active substance in concentrations of from 0.01 ppm to 100%, preferably from 0.01 ppm to 10%.

Parenteral formulations are injections in the form of solutions, emulsions and suspensions, as well as implants.

The active substances may be present in the formulations on their own or mixed with other active substances, mineral salts, trace elements, vitamins, proteins, colourings, fats or flavourings.

The concentration of the active substances in the feed is normally about 0.01 to 500 ppm, preferably 0.1 to 50 ppm.

The active substances may be added to the feed as such or in the form of premixes or food concentrates.

Thus, the feedstuff according to the invention contains, in addition to the active substance and possibly a conventional vitamin/mineral mixture, for example for pig feeds: barley, wheat bran, broad beans, rape extract groats and edible fat, and for broilers: maize, soya bean flour, meatmeal, edible fat and soya oil, and for cattle: shredded sugar beet, maize gluten, malt germs, soya bean flour, wheat and molasses and for lambs: barley, soya bean flour, maize and molasses. To this feed is added one of the above-mentioned compounds of formula I as active substance in a concentration of 0.1 to 500 ppm, but preferably 0.1 to 50 ppm, the active substance preferably being added in the form of a premix. This premix contains for example, 10 mg of active substance per 10 g, preferably in 9.99 g of corn starch.

The Examples which follow are intended to the illustrate the invention:

PREPARATION OF THE STARTING COMPOUNDS

Example A

Ethyl 4'-acetonyl-biphenylyl-4-carboxylate a) Ethyl 4'-(2-chloro-propionyl)biphenylyl-4-carboxylate A solution of 10 g (0.044 mol) of ethyl biphenylyl-4-carboxylate in 70 ml of methylene chloride is added dropwise at 0° C. to a solution of 25 g (0.187 mol) of aluminium chloride and 9.6 g (0.076 mol) of 2-chloro-propionylchloride in 250 ml of methylene chloride. After standing overnight at ambient temperature it is added to ice water and dilute hydrochloric acid and extracted with methylene chloride. The extracts are dried and, after concentration by evaporation, purified by column chromatography using cyclohexane/ethyl acetate (7:1) as eluant. 6.9 g of ethyl 4'-(2-chloro-propionyl)biphenylyl-4-carboxylate are obtained.

Melting point: 75°–78° C.

b) 6.8 g (0.021 mol) of ethyl 4'-(2-chloro-propionyl)-biphenylyl-4-carboxylate are refluxed for two days in 40 ml of acetone with 3.9 g (0.034 mol) of potassium acetate. Then the precipitate is filtered off, the filtrate is evaporated down and the evaporation residue is purified by column chromatography (eluant: cyclohexane/ethyl acetate=7:1). 5.5 g of ethyl 4'-(2-acetoxy-propionyl)-biphenylyl-4-carboxylate are obtained.

c) 5.5 g (0.016 mol) of ethyl 4'-(2-acetoxy-propionyl)-biphenylyl-4-carboxylate are dissolved in 160 ml of ethanol and at 5° to 10° C. sodium borohydride is added in batches (about 1 g) until no further starting material can be detected in the chromatogram. Then the mixture is evaporated down, decomposed with water and extracted with ethyl acetate. The extracts are concentrated by evaporation and after the addition of 50 g of polyphosphoric acid, they are stirred in an oil bath at 80° C. The mixture is poured onto ice water and extracted with ethyl acetate. The extracts are dried, concentrated by evaporation and purified by column chromatography on silica gel. (Eluant: cyclohexane/ethyl acetat =3:1).

Yield: 2.8 g (62% of theory)
Melting point: 71°–73° C.

The following are obtained analogously to Example A:
4'-acetonyl-4-methoxy-biphenyl,
Melting point: 89°–92° C.
4'-acetonyl-2-methoxy-biphenyl,
Melting point: less than 20° C.
ethyl 4'-acetonyl-biphenylyl-2-carboxylate,
Melting point: less than 20° C.
ethyl 4'-acetonyl-diphenylmethane-2-carboxylate,
4'-acetonyl-4-chloro-biphenyl,
Melting point: 74°–76° C.
ethyl 4'-acetonyl-1,2-diphenylethane-2-carboxylate.

Example B

4'-Acetonyl-4-hydroxy-biphenyl 4 8 g (20 mmol) of 4'-acetonyl-4-methoxy-biphenyl are dissolved in 50 ml of benzene and after the addition of 6.14 g (46 mmol) of aluminium chloride refluxed for 24 hours. It is then poured onto ice and dilute hydrochloric acid, extracted with chloroform and the extracts are purified by silica gel chromatography (eluant: toluene/ethyl acetate =6:1).

Yield: 2.8 g (62% of theory),
Melting point: 151°–153° C.

The following is obtained analogously to Example B:
4'-acetonyl-2-hydroxy-biphenyl

Example C

Methyl 4'-acetonyl-biphenylyl-2-oxyacetate 4.3 g (19 mmol) of 4'-acetonyl-2-hydroxy-biphenyl are dissolved in 50 ml of acetone and after the addition of 2.63 g (19 mmol) of potassium carbonate and 1.8 ml (19 mmol) of methylbromoacetate the mixture is refluxed for 5 hours. It is then filtered, the filtrate is concentrated by evaporation and the residue is chromatographed on silica gel (eluant: toluene/ethyl acetate=10:1).

Yield: 5.0 g (88.2% of theory),
Melting point: less than 20° C.

The following is obtained analogously to Example C:
methyl 4'-acetonyl-biphenylyl-4-oxyacetate
Melting point: 81°–82° C.

Example D

4'-(2-Amino-propyl)-4-ethyl-biphenyl a) 9.0 g (0.0426 mol) of 4-(2-amino-propyl)biphenyl are dissolved in 50 ml of glycol and after the addition of 6.3 g (0.0426 mol) of phthalic acid anhydride the mixture is stirred for 2 hours at 170° C. It is then diluted with water and the 4-(2-phthalimido-propyl)biphenyl is extracted with ethyl acetate. After concentration of the extracts by evaporation and crystallisation from methanol, 10.4 g (72% of theory) are obtained, melting point 143°–145° C.

b) 3 g (8.8 mmol) of 4-(2-phthalimido-propyl)biphenyl are placed in 50 ml of carbon disulphide and after the addition of 4 g (0.03 mol) of aluminium chloride, 0.78 g (0.01 mol) of acetylchloride are added dropwise After standing overnight, the mixture is poured onto ice water/dilute hydrochloric acid and extracted with chloroform. By concentration of the extracts by evaporation and crystallisation from acetone, 1.58 g (47% of theory) of 4'-(2-phthalimido-propyl)-4-acetyl-biphenyl are obtained, melting point 157°–159° C.

c) 1.0 g (2.6 mmol) of 4'-(2-phthalimido-propyl)-4-acetyl-biphenyl are stirred into 25 ml of glycol with 0.5 ml of hydrazine hydrate and 0.9 g (0.016 mol) of potassium hydroxide for 3 hours at 200° C. The mixture is then diluted with water, extracted with ether and the extracts are concentrated by evaporation.

Yield: 0.56 g (90% of theory).

The following is obtained analogously to Example D:
4'-(2-Amino-ethyl)-4-ethyl-biphenyl By hydrazinolysis of the corresponding phthalimido compounds, the following are obtained analogously to Example Dc:
4'-(2-amino-ethyl)-4-methoxy-biphenyl and
4'-(2-amino-propyl)-4-methoxy-biphenyl

Example E

Ethyl 4'-(2-amino-propyl)biphenylyl-4-carboxylate a) 0.9 g (2.3 mmol) of 4'-(2-phthalimido-propyl)-4-acetyl-biphenyl (Example Db) are suspended in 10 ml of dioxan and 10 ml of water and after the addition of 0.96 g (24 mmol) of powdered sodium hydroxide, with cooling, 1.43 g (9 mmol) of bromine are added dropwise. The mixture is stirred for another hour, acidified with hydrochloric acid and suction filtered to remove the precipitate. 0.8 g (90.3% of theory) of 4'-(2-phthalimido-propyl)biphenylyl-4-carboxylic acid are obtained, melting point 280° C.

b) 2.0 g (5.2 mmol) of the compound described above are suspended in 50 ml of concentrated hydrochloric acid and shaken in a pressurised vessel at 120° C. for 6 hours. Then the suspension is evaporated to dryness, digested with warm acetone and suction filtered to remove the precipitate. The precipitate is dissolved in ethanol and refluxed for 2 hours whilst dry hydrochloric acid gas is piped in. It is then evaporated down, made alkaline and extracted with ethyl acetate. After the extracts have been evaporated down, 0.6 g (41% of theory) of ethyl 4'-(2-amino-propyl)bi-phenylyl-4-carboxylate are obtained.

The following is obtained analogously to Example E:
ethyl 4'-(2-amino-ethyl)biphenylyl-4-carboxylate

Example F

4-(2-Amino-pentyl)biphenyl a) 9.11 g (50 mmol) of biphenylyl-4-aldehyde are mixed with 7.4 ml of butylamine in 100 ml of toluene and boiled for 2 hours using a water separator. The mixture is then evaporated down, taken up in 100 ml of glacial acetic acid and after the addition of 10 g (0.096 mol) of nitrobutane, the mixture is stirred for 1 hour at 100° C. It is then evaporated down and recrystallised from isopropanol.

Yield: 85.0% of theory,
Melting point: 67°-69° C.

b) 11.9 g (0.044 mol) of the nitro-olefin described above are dissolved in 50 ml of tetrahydrofuran and added dropwise to a boiling suspension of 3.8 g (0.1 mol) of lithium aluminium hydride in 100 ml of tetrahydrofuran. The mixture is stirred for a further hour, then decomposed with 4N sodium hydroxide solution, filtered from the sodium aluminate and the filtrate is evaporated down. The base thus obtained is converted into the hydrochloride by the addition of ethanol/ethanolic hydrochloric acid.

Yield: 80% of theory,
Melting point: 204°-206° C.

Analogously to Example F, using nitromethane or nitroethane, the following are obtained:
  4-(2-amino-ethyl)biphenyl,
  4-(2-amino-propyl)biphenyl,
  4'-(2-amino-ethyl)-4-methoxy-1,2-diphenylethane,
  4'-(2-amino-propyl)-4-methoxy-1,2-diphenylethane,
  4'-(2-amino-ethyl)-4-methoxy-diphenylmethane,
  4'-(2-amino-ethyl)-4-methoxy-biphenyl.

Example G

4-(2-Amino-ethyl)diphenylmethane

Prepared by Friedel-Crafts acylation of N-acetyl-2-phenyl-ethylamine with benzoylchloride, subsequent hydrolysis to obtain the 4-(2-amino-ethyl)benzophenone and subsequent Wolff-Kishner reduction with hydrazine (see J. Amer. Chem. Soc. 76, 5623 (1954)).

The following are obtained analogously to Example G:
  4'-(2-amino-propyl)-4-methyl-diphenylmethane,
  4-(2-amino-propyl)-diphenylmethane,
  4'-(2-amino-propyl)-4-chloro-diphenylmethane,
  4'-(2-amino-ethyl)-4-methyl-diphenylmethane,
  4'-(2-amino-ethyl)-4-chloro-diphenylmethane,
  Ethyl 4'-(2-amino-ethyl)diphenylmethane-2-carboxylate (by subsequent esterification of 4'-(2-amino-ethyl)-diphenylmethane-2-carboxylic acid),
  ethyl 4'-(2-amino-ethyl)diphenylmethane-4-carboxylate (by subsequent esterification of 4'-(2-amino-ethyl)-diphenylmethane-4-carboxylic acid).

Example H

Methyl 4'-(2-amino-ethyl)diphenylmethane-2-oxyacetate a) 15.7 g (0.053 mol) of phenyl 4-[2-(ethoxycarbonylamino)ethyl]benzoate are dissolved in 80 ml of chlorobenzene and after the addition of 25 g (0.094 mol) of aluminium bromide, stirred for 5 hours at 110° C. The mixture is then poured onto ice/hydrochloric acid and extracted with methylene chloride. By column chromatography on silica gel using cyclohexane/ethyl acetate=3:1 as eluant, the 4'-[2-(ethoxycarbonylamino)ethyl]-2-hydroxybenzophenone is obtained in a 46% yield.

b) 6.5 g (0.021 mol) of the compound described hereinbefore are stirred into 50 ml of glycol for 4 hours at 180° C. after the addition of 7.1 g (0.127 mol) of potassium hydroxide and 4.1 g of hydrazine hydrate. This is then poured onto ice/hydrochloric acid, made alkaline with ammonia, extracted with chloroform and concentrated by evaporation. After silica gel chromatography using chloroform/methanol/methanolic ammonium (5:1:0.1) as eluant, 4'-(2-amino-ethyl)-2-hydroxy-diphenylmethane is obtained in a 26% yield.

c) 11.5 g (0.05 mol) of the above amine are placed in 60 ml of dioxan and 60 ml of 2N sodium hydroxide solution and, whilst cooling with ice, 12 g (0.07 mol) of benzyl chloroformate are added dropwise. After standing overnight the mixture is acidified, extracted with chloroform and, after evaporation of the extracts, chromatographed on silica gel (eluant: toluene/ethyl acetate=14:1). 55% of 4'-[2-(benzyloxycarbonylamino)ethyl]-2-hydroxy-diphenylmethane are obtained.

d) 5 g (0.014 mol) of the compound described above are refluxed for 3 hours in acetone with 1.9 g (0.014 mol) of potassium carbonate and 2.1 g (0.014 g) of methyl bromoacetate. The mixture is then filtered, concentrated by evaporation and chromatographed on silica gel using chloroform as eluant. The methyl 4'-[2-(benzyloxycarbonyl-amino)ethyl]diphenylmethane-2-oxyacetate thus isolated is then hydrogenated in 40 ml of methanol, at ambient temperature and under a hydrogen pressure of 5 bar, after the addition of 8 ml of saturated methanolic hydrochloric acid and 0.4 g of 10% palladium on charcoal. After the uptake of hydrogen has ceased the catalyst is filtered off and the filtrate is concentrated by evaporation. 1.9 g of methyl 4'-(2-amino-ethyl)diphenylmethane-2-oxyacetate hydrochloride are obtained.

The following is obtained analogously to Example H:
  4'-(2-Amino-ethyl)-2-methoxy-diphenylmethane-hydrochloride

Example 1

Ethyl 4'-[2-[N-(2-(3-chloro-phenyl)-2-hydroxy-ethyl)amino]-propyl]biphenylyl-4-carboxylate 5.6 g (20 mmol) of ethyl 4'-acetonyl-biphenylyl-4-carboxylate and 3.4 g (20 mmol) of 2-(3-chlorophenyl)-2-hydroxy-ethylamine are dissolved in 75 ml of ethanol and after the addition of 1.25 g (20 mmol) of sodium cyanoborohydride and 1.2 ml (20 mmol) of glacial acetic acid, the mixture is stirred for 24 hours at ambient temperature. It is then concentrated by evaporation, added to water and acidified with dilute hydrochloric acid. After 30 minutes' stirring it is made alkaline with sodium hydroxide solution and extracted with ethyl acetate. The extracts are concentrated by evaporation and the evaporation residue is purified by column chromatography on silica gel (eluant: ethyl acetate/methanol=40:1). It is then recrystallised from acetonitrile.

Yield: 4.3 g (49% of theory),
Melting point: 104°-116° C.
Calculated: C 71.30 H 6.44 N 3.20 Cl 8.10
Found: 71.45 6.30 3.47 8.08
According to $^1$H-NMR (400 MHz) there is a 1:1 mixture of pairs of diastereoisomers.
[CDCl$_3$: delta=4.56 ppm (dd, 0.5 H), delta=4.62 ppm (dd, 0.5 H)]

The following compounds are prepared analogously to Example 1:

a) 4'-Hydroxy-4-[2-[N-(2-hydroxy-2-phenyl-ethyl)amino]propyl]biphenyl-hydrochloride Prepared from 2-hydroxy-2-phenyl-ethylamine and 4'-acetonyl-4-hydroxy-biphenyl.

Yield: 50% of theory,
Melting point: 154°–156° C.
Calculated: C 71.95 H 6.83 N 3.65
Found: 71.77 6.79 3.61

According to $^1$H-NMR (400 MHz) there is a 1:1 mixture of pairs of diastereoisomers.

b) Methyl 4'-[2-[N-(2-hydroxy-2-phenyl-ethyl)amino]propyl]biphenylyl-4-oxyacetate Prepared from 2-hydroxy-2-phenylethylamine and methyl 4'-acetonyl-biphenylyl-4-oxyacetate.

Yield: 23% of theory,
Melting point: 90°–91° C.
Calculated: C 74.44 H 6.97 N 3.34
Found: 74.31 7.13 3.03

According to $^1$H-NMR (400 MHz) there is a 2:3 mixture of pairs of diastereoisomers.

[CDCl$_3$: delta=4.60 ppm (dd, 0.6 H), delta=4.66 ppm (dd, 0.4 H)]

c) 4'-[2-[N-(3-Chloro-phenyl)-2-hydroxy-ethyl)amino]propyl]-4-hydroxy-biphenyl Prepared from 2-(3-chloro-phenyl)-2-hydroxy-ethylamine and 4'-acetonyl-4-hydroxy-biphenyl.

Yield: 41% of theory,
Melting point: 97°–99° C.
Calculated: C 72.34 H 6.33 N 3.67
Found: 72.17 6.59 3.88

According to $^1$H-NMR (400 MHz) there is a 5:3 mixture of pairs of diastereoisomers.

[CDCl$_3$: delta=4.60 ppm (dd, 0.62 H), delta=4.66 ppm (dd, 0.38 H)]

d) Methyl 4'-[2-[N-(2-(3-chloro-phenyl)-2-hydroxyethyl)amino]propyl]biphenylyl-4-oxyacetate Prepared from 2-(3-chloro-phenyl)-2-hydroxy-ethylamine and methyl 4'-acetonyl-biphenylyl-4-oxyacetate.

Yield: 25% of theory,
Melting point: 106°–109° C.
Calculated: C 68.79 H 6.22 N 3.09 Cl 7.81
Found: 68.90 6.06 3.07 7.62

According to $^1$H-NMR (400 MHz) there is a 1:1 mixture of pairs of diastereoisomers.

[CDCl$_3$ delta=4.55 ppm (dd), delta=4.615 ppm (dd)]

e) 4'-[2-[N-(2-(3-Chloro-phenyl)-2-hydroxy-ethyl)amino]propyl]-4-methoxy-biphenyl Yield: 20.1% of theory, Prepared from 2-(3-chlorophenyl)-2-hydroxy-ethylamine and 4'-acetonyl-4-methoxy-biphenyl.

Melting point: 109°–111° C.
Calculated: C 72.81 H 6.62 N 3.54 Cl 8.95
Found: 72.80 6.64 3.57 8.82

According to $^1$H-NMR (400 MHz) there is a 1:3 mixture of pairs of diastereoisomers.

[CDCl$_3$: delta=4.55 ppm (dd, 0.75 H), delta=4.62 ppm (dd, 0.25 H)]

f) 4'-Chloro-4-[2-[N-(2-(3-chloro-phenyl)-2-hydroxyethyl)amino]propyl]biphenyl Prepared from 4'-acetonyl-4-chloro-biphenyl and 2-(3-chloro-phenyl)-2-hydroxy-ethylamine.

Yield: 26% of theory,
Melting point: 115°–117° C.
Calculated: C 69.00 H 5.79 N 3.50 Cl 17.71
Found: 69.10 5.74 3.34 17.98

According to $^1$H-NMR (400 MHz) there is a 3:4 mixture of pairs of diastereoisomers.

[CDCl$_3$: delta=4.56 ppm (dd, 0.57 H), delta=4.62 ppm (dd, 0.43 H)]

g) Ethyl 4'-[2-[N-(2-hydroxy-2-phenyl-ethyl)amino]propyl]-biphenylyl-4-carboxylate Prepared from 2-hydroxy-2-phenyl-ethylamine and ethyl 4'-acetonyl-biphenylyl-4-carboxylate.

Yield: 62.5% of theory,
Melting point: 96°–98° C.
Calculated: C 77.39 H 7.24 N 3.47
Found 77.20 7.08 3.29

According to $^1$H-NMR (400 MHz) there is a 1:1 mixture of pairs of diastereoisomers.

[CDCl$_3$: delta=4.62 ppm (dd, 0.5 H), delta=4.67 ppm (dd, 0.5 H)]

h) Ethyl 4'-[2-[N-(2-(3-chloro-phenyl)-2-hydroxyethyl)amino]propyl]-biphenylyl-2-carboxylate Prepared from 2-(3-chloro-phenyl)-2-hydroxy-ethylamine and ethyl 4'-acetonyl-biphenylyl-2-carboxylate.

Yield: 39.3% of theory,
Melting point: less than 20° C.
Calculated: C 71.30 H 6.44 N 3.20
Found 71.55 6.27 3.09

According to $^1$H-NMR (400 MHz) there is a 1:1 mixture of pairs of diastereoisomers.

[CDCl$_3$: delta=4.50 ppm (dd, 0.5 H), delta=4.60 ppm (dd, 0.5 H)]

i) 4'-[2-[N-(2-(3-Chloro-phenyl)-2-hydroxy-ethyl)amino]propyl]-2-methoxy-biphenyl Prepared from 2-(3-chloro-phenyl)-2-hydroxy-ethylamine and 4'-acetonyl-2-methoxy-biphenyl.

Yield: 88.4% of theory,
Melting point: less than 20° C.
Calculated: C 72.81 H 6.62 N 3.54
Found: 72.61 6.60 3.62

According to $^1$H-NMR (400 MHz) there is a 1:1 mixture of pairs of diastereoisomers.

[CDCl$_3$: delta=4.61 ppm (dd, 0.5 H), delta=4.55 ppm (dd, 0.5 H)]

k) Methyl 4'-[2-[N-(2-(3-chloro-phenyl)-2-hydroxyethyl)amino]propyl]-biphenylyl-2-oxyacetate. Prepared from 2-(3-chloro-phenyl)-2-hydroxy-ethylamine and methyl 4'-acetonyl-biphenylyl-2-oxyacetate.

Yield: 83% of theory,
Melting point: less than 20° C.
Calculated: C 68.79 H 6.22 N 3.08
Found: 68.80 6.10 2.91

According to $^1$H-NMR (400 MHZ) there is a 1:1 mixture of pairs of diastereoisomers.

[CDCl$_3$: delta=4.686 ppm (dd, 0.5 H), delta=4.62 ppm (dd, 0.5 H)]

l) Ethyl 4'-[2-[N-(2-(3-chloro-phenyl)-2-hydroxyethyl)amino]propyl]-1,2-diphenylethane-2-carboxylate Prepared from 2-(3-chloro-phenyl)-2-hydroxy-ethylamine and ethyl 4'-acetonyl-1,2-diphenylethane 2-carboxylate.

Yield: 67% of theory,
Melting point: less than 20° C.
Calculated: C 72.16 H 7.12 N 3.01 Cl 7.61
Found: 72.40 7.18 2.93 7.41

According to $^1$H-NMR (400 MHz) there is a 1:1 mixture of pairs of diastereoisomers.

[CDCl$_3$: delta=4.54 ppm (dd, 0.5 H), delta=4.62 ppm (dd, 0.5 H)]

m) Ethyl 4'-[2-[N-(2-(3-chloro-phenyl)-2-hydroxyethyl)amino]propyl]diphenylmethane-2-carboxylate Prepared from 2-(3-chloro-phenyl)-2-hydroxy-ethylamine and ethyl 4'-acetonyl-diphenylmethane-2-carboxylate.

Yield: 83% of theory,
Melting point: less than 20° C.
Calculated: C 71.75 H 6.69 N 3.10 Cl 7.84
Found: 71.45 6.87 2.94 8.03

According to $^1$H-NMR (400 MHz) there is a 1:1 mixture of pairs of diastereoisomers.

[CDCl3: delta=4.51 ppm (dd, 0.5 H), delta=4.59 ppm (dd, 0.5 H)]

Example 2

4'-[2-[N-(2-Hydroxy-2-phenyl-ethyl)amino]ethyl]-4-methoxy-biphenyl 4 g (20 mmol) of phenacylbromide are dissolved in 20 ml of methylene chloride and added dropwise to a solution of 4.6 g (20 mmol) of 4'-(2-aminoethyl)-4-methoxy-biphenyl and 3.45 ml (20 mmol) of N,N-diisopropyl-ethylamine and 100 ml of methylene chloride at ambient temperature. After 2 hours, 50 ml of methanol are added and, with slight cooling, 1 g (27 mmol) of sodium borohydride is added in batches. After stirring overnight the mixture is evaporated in vacuo, acidified with dilute hydrochloric acid and stirred for 30 minutes. It is then made alkaline with sodium hydroxide solution and extracted with chloroform. The chloroform evaporation residue is purified by column chromatography on silica gel (eluant: chloroform/methanol = 10:1). Finally, it is recrystallised from acetonitrile.

Yield: 1.1 g (16% of theory),
Melting point: 137°-138° C.
Calculated: C 79.51 H 7.25 N 4.03
Found: 79.62 7.19 3.97

The following compounds are prepared analogously to Example 2:

a) 4'-[2-[N-(2-(3-Chloro-phenyl)-2-hydroxy-ethyl)amino]ethyl]-4-hydroxy-biphenyl-semihydrate Prepared from 3-chloro-phenacylbromide and 4'-(2-amino-ethyl)-4-hydroxy-biphenyl.

Yield: 13% of theory,
Melting point: 114°-117° C.
Calculated: C 70.09 H 6.15 N 3.72
Found: 69.90 6.11 3.74 b) 4'-[2-[N-(2-(3-Chloro-phenyl)-2-hydroxy-ethyl)amino]ethyl]-4-methoxy-biphenyl Prepared from 3-chloro-phenacylbromide and 4'-(2-amino-ethyl)-4-methoxy-biphenyl.

Yield: 34% of theory,
Melting point: 114°-116° C.
Calculated: C 72.34 H 6.33 N 3.67 Cl 9.28
Found: 72.40 6.17 3.53 9.08 c) Ethyl 4'-[2-[N-(2-(3-chloro-phenyl)-2-hydroxyethyl)amino]ethyl]-biphenylyl-4-carboxylate From 3-chloro-phenacylbromide and ethyl 4'-(2-aminoethyl)-biphenylyl-4-carboxylate.

Yield: 14% of theory,
Melting point: 121°-122° C.
Calculated: C 70.83 H 6.18 N 3.30 Cl 8.36
Found: 70.90 6.19 3.35 8.39 d) 4-[2-[N-(2-(3-Chloro-phenyl)-2-hydroxy-ethyl)amino]propyl]biphenyl Prepared from 3-chloro-phenacylbromide and 4-(2-amino-propyl)biphenyl.

Yield: 23% of theory,
Melting point 95°-96° C.
Calculated: C 75.50 H 6.61 N 3.89
Found 75.70 6.69 3.93

According to $^1$H-NMR (400 MHz) there is a 1:2 mixture of pairs of diastereoisomers.

[CDCl3: delta=4.57 ppm (dd, 0.66 H), delta=4.63 ppm (dd, 0.33 H)]

e) 4'-[2-[N-(2-(3-Chloro-phenyl)-2-hydroxy-ethyl)amino]propyl-4-ethyl-biphenyl Prepared from 4'-(2-amino-propyl)-4-ethyl-biphenyl and 3-chloro-phenacylbromide Yield: 26% of theory,
Melting point: 104°-114° C.
Calculated: C 76.22 H 7.16 N 3.56 Cl 9.00
Found: 76.37 7.30 3.53 9.12

According to $^1$H-NMR (400 MHz) there is a 2:1 mixture of pairs of diastereoisomers.

[CDCl3: delta=4.56 ppm (dd, 0.33 H), delta=4.62 ppm (dd, 0.66 H)]

f) Ethyl 4'-[2-[N-(2-(3-chloro-phenyl)-2-hydroxyethyl)amino]propyl]biphenylyl-4-carboxylate Prepared from ethyl 4'-(2-amino-propyl)biphenylyl-4-carboxylate and 3-chloro-phenacylbromide.

Yield: 25% of theory,
Melting point: 94°-96° C.
Calculated: C 71.30 H 6.44 N 3.20
Found: 71.45 6 52 3.37

According to [1]H-NMz (400 MHZ) there is a 1:2 mixture of pairs of diastereoisomers.

[CDCl3: delta=4.56 ppm (dd, 0.33 H), delta=4.62 ppm (dd, 0.66 H)]

g) 4-[2-[N-(2-(3-Chloro-phenyl)-2-hydroxy-ethyl)amino]ethyl]biphenyl Prepared from 3-chloro-phenacylbromide and 4-(2-amino-ethyl)-biphenyl.

Yield: 23% of theory,
Melting point: 109°-110° C.
Calculated: C 75.10 H 6.30 N 3.98 Cl 10.07
Found: 74.99 6.30 3.97 10.28 h) 4'-[2-[N-(2-(3 chloro-phenyl)-2-hydroxy-ethyl)amino]ethyl]-4-ethyl-biphenyl Prepared from 3-chloro-phenacylbromide and 4'-(2-amino-ethyl)-4-ethyl-biphenyl.

Yield: 23% of theory,
Melting point: 123°-125° C.
Calculated: C 75.97 H 6.90 N 3.69 Cl 9.33
Found: 75.95 6.78 3.58 9.37 i) 4-[2-[N-(2-(3-Chloro-phenyl)-2-hydroxy-ethyl)amino]ethyl]diphenylmethane Prepared from 4-(2-amino-ethyl)diphenylmethane and 3-chloro-phenacylbromide.

Yield: 49% of theory,
Melting point: 86°-87° C.
Calculated: C 75.50 H 6.61 N 3.83 Cl 9.69
Found: 75.74 6.41 3.96 9.53 j) 4'-[2-[N-(2-(3-Chloro-phenyl)-2-hydroxy-ethyl)amino]ethyl]-4-methoxy-diphenylmethane Prepared from 3-chloro-phenacylbromide and 4'-(2-amino-ethyl)-4-methoxy-diphenylmethane.

Yield: 22.5% of theory,
Melting point: 90°-92° C.
Calculated: C 72.81 H 6.62 N 3.54 Cl 8.95
Found: 72.66 6.51 3.53 8.93 k) 4'-[2-[N-(2 (3-Chloro-phenyl)-2-hydroxy-ethyl)amino]ethyl]-4-methyl-diphenylmethane Prepared from 3-chloro-phenacylbromide and 4'-(2-amino-ethyl)-4 methyl-diphenylmethane.

Yield: 25.5% of theory,
Melting point: 100°-102° C.
Calculated: C 75.87 H 6.90 N 3.69 Cl 9.33
Found: 75.56 6.94 3.77 9.43 l) Ethyl 4'-[2-[N-(2-(3-chloro-phenyl)-2-hydroxyethyl)amino]ethyl]diphenylmethane-4-carboxylate Prepared from 3-chloro-phenacylbromide and ethyl 4'-(2-amino-ethyl)-diphenylmethane-4-carboxylate.

Yield: 19% of theory,
Melting point: 97°-98° C.
Calculated: C 70.97 H 6.39 N 3.20 Cl 8.09
Found: 71.14 6.44 3.29 8.14 m) 4'-Chloro-4-[2-[N-(2-(3-chloro-phenyl)-2-hydroxyethyl)amino]ethyl]diphenylmethane Prepared from 4'-(2-amino-ethyl)-4-chloro-diphenylmethane and 3-chloro-phenacylbromide.

Yield: 16% of theory,
Melting point: 86°-88° C.
Calculated: C 69.01 H 5.79 N 3.50 Cl 17.71
Found 69.11 5.72 3.45 17.66 n) 4-[2-[N-(2-Hydroxy-2-phenyl-ethyl)amino]propyl]diphenylmethane Prepared from 4-(2-aminopropyl)diphenylmethane and phenacylbromide.

Yield: 17% of theory,
Melting point: 86°-88° C.
Calculated: C 83.44 H 7.88 N 4.05
Found: 83.35 8.03 4.06

According to $^1$H-NMR (400 MHz) there is a 45:55 mixture of pairs of diastereoisomers.

[CDCl$_3$: delta=4.57 ppm (dd, 0.45 H), delta=4.64 ppm (dd, 0.55 H)]

o) 4-[2-[N-(2-(3-Chloro-phenyl)-2-hydroxy-ethyl)amino]propyl]diphenylmethane Prepared from 4-(2-amino-propyl)diphenylmethane and 3-chloro-phenacylbromide.

Yield: 17.9% of theory,
Melting point: 92°-96° C.
Calculated: C 75.87 H 6.80 N 3.69 Cl 9.33
Found 75.70 6.97 3.57 9.46

According to $^1$H-NMR (400 MHz) there is a 1:1 mixture of pairs of diastereoisomers.

[CDCl$_3$: delta=4.52 pm (dd), delta=4.58 ppm (dd)]

p) 4'-Chloro-4-[2-[N-(2-(3-chloro-phenyl)-2-hydroxyethyl)amino]propyl]diphenylmethane Prepared from 3-chloro-phenacylbromide and 4'-(2-amino-propyl)-4-chloro-diphenylmethane.

Yield: 19.2% of theory,
Melting point: 85°-90° C.
Calculated: C 69.57 H 6.08 N 3.38 Cl 17.11
Found 69.70 6.01 3.26 17.24

According to $^1$H-NMR (400 MHz) there is a 20:1 mixture of pairs of diastereoisomers.

[CDCl$_3$: delta=4.54 ppm (dd, 0.05 H), delta=4.61 ppm (dd, 0.95 H)]

q) Ethyl 4'-[2-[N-(2-hydroxy-2-phenyl-ethyl)amino]ethyl]benzhydrol-4'-carboxylate Prepared from phenacylbromide and ethyl 4'-(2-aminoethyl)benzophenone-4-carboxylate.

Yield: 14.6% of theory,
Melting point: 111°-113° C.
Calculated: C 74.80 H 6.52 N 3.35
Found: 75.00 6.65 3.49 r) 4-[2-[N-(2-(3-Chloro-phenyl)-2-hydroxy-ethyl)amino]-2-methyl-propyl]biphenyl Prepared from 3-chloro-phenacylbromide and 4-(2-amino-2-methylpropyl)biphenyl.

Yield: 13% of theory,
Melting point: 80° C.
Calculated: C 75.87 H 6.90 N 3.69 Cl 9.33
Found: 76.00 6.96 3.68 9.25 s) 4-[2-[N-(2-(3-Chloro-phenyl)-2-hydroxy-ethyl)amino]pentyl]biphenyl-hydrochloride Prepared from 3-chloro-phenacylbromide and 4-(2-amino-pentyl)-biphenyl-hydrochloride.

Yield: 11.5% of theory,
Melting point: 164°-167° C.
Calculated: C 69.77 H 6.79 N 3.25 Cl 16.48
found: 69.74 6.74 3.21 16.45

According to $^1$H-NMR (400 MHz) there is a 2:1 mixture of pairs of diastereoisomers.

[CDCl$_3$/CD$_3$OD: delta=5.10 ppm (dd, 0.66 H), delta=5.17 ppm (dd, 0.33 H)]

t) 4'-[2-[N-(2-(4-Amino-3-cyano-5-fluoro-phenyl)-2-hydroxy-ethyl)amino]ethyl]-4-methoxy-biphenyl Prepared from 4-amino-3-cyano-5-fluoro-phenacylbromide and 4'-(2-amino-ethyl)-4-methoxy-biphenyl.

Yield: 22.3% of theory,
Melting point: 150°-153° C.
Calculated: C 71.09 H 5.97 N 10.36
Found: 70.93 5.91 10.24 u) Ethyl 4'-[2-[N-(2-(4-amino-3-cyano-5-fluoro-phenyl)-2-hydroxy-ethyl)amino]ethyl]biphenylyl-4-carboxylate Prepared from 4-amino-3-cyano-5-fluoro-phenacylbromide and ethyl 4'-(2-amino-ethyl)biphenylyl-4-carboxylate.

Yield: 18% of theory,
Melting point: 153°-154° C.
Calculated: C 69.78 H 5.86 N 9.39
Found: 69.59 5.64 9.23 v) Ethyl 4'-[2-[N-(2-(4-amino-3,5-dichloro-phenyl)-2-hydroxy-ethyl)-amino]ethyl]biphenylyl-4-carboxylate Prepared from 4-amino-3,5-dichloro-phenacylbromide and ethyl 4'-(2-amino-ethyl)biphenylyl-4-carboxylate.

Yield: 17.6% of theory,
Melting point: 123°-125° C.
Calculated: C 63.70 H 5.13 N 5.94 Cl 15.04
Found: 63.78 5.24 5.95 15.22 w) 4'-[2-[N-(2-(4-Amino-3,5-dichloro-phenyl)-2-hydroxy-ethyl)-amino]ethyl]-4-methoxy-biphenyl Prepared from 4-amino-3,5-dichloro-phenacylbromide and 4'-(2-amino-ethyl)-4-methoxy-biphenyl.

Yield: 17% of theory,
Melting point: 150°-151° C.
Calculated: C 64.04 H 5.61 N 6.49 Cl 16.44
Found: 64.17 5.78 6.45 16.44 x) 4'-[2-N-(2-(4-Amino-3,5-dichloro-phenyl)-2-hydroxy-ethyl)-aminoethyl]-4-hydroxy-biphenyl Prepared from 4-amino-3,5-dichloro-phenacylbromide and 4'-(2-amino-ethyl)-4-hydroxy-biphenyl.

Yield: 11% of theory,
Melting point: 88°-90° C.
Calculated: C 63.32 H 5.31 N 6.71 Cl 16.99
Found: 63.35 5.58 6.81 16.63 y) Ethyl 4'-[2-[N-(2-(3-chloro-phenyl)-2-hydroxyethyl)amino]ethyl]diphenylmethane-2-carboxylate Prepared from 3-chloro-phenacylbromide and ethyl 4'-(2-amino-ethyl)-diphenylmethane-2-carboxylate.

Yield: 30.4% of theory,
Melting point: less than 20° C.
Calculated: C 71.30 H 6.44 N 3.20
Found: 71.36 6.44 3.37 z) 4'-2-[N-(2-(3-Chloro-phenyl)-2-hydroxy-ethyl)amino]propyl]4-methoxy-1,2-diphenylethane Prepared from 3-chloro-phenacylbromide and 4'-(2-aminopropyl)-4-methoxy-1,2-diphenylethane.

Yield: 17% of theory,
Melting point: 108°-110° C.
Calculated C 73.65 H 7.13 N 3.30 Cl 8.36
Found: 73.45 7.19 3.50 8.40

According to ¹H-NMR (400 MHz) there is a 4:1 mixture of pairs of diastereoisomers.

[CDCl₃/CD₃OD: delta=4.59 ppm (dd, 0.8 H), delta=4.52 ppm (dd, 0.2 H)]

aa) 4'-[2-[N-(2-(3-Chloro-phenyl)-2-hydroxy-ethyl)amino]ethyl]-4-methoxy-1,2-diphenylethane Prepared from 3-chloro-phenacylbromide and 4'-(2-amino-ethyl)-4-methoxy-1,2-diphenylethane.

Yield: 27.8% of theory,
Melting point: 112°–113° C.
Calculated: C 73.24 H 6.88 N 3.42 Cl 8.65
Found: 73.45 6.92 3.28 8.60 ab) Methyl 4'-[2-[N-(2-(3-chloro-phenyl)-2-hydroxyethyl)amino]ethyl]diphenylmethane-2-oxyacetate Prepared from 3-chloro-phenacylbromide and ethyl 4'-(2-amino-ethyl)-diphenylmethane-2-oxyacetatehydrochloride with the addition of N,N-diisopropylethylamine.

Yield: 14% of theory,
Melting point: 84°–86° C.
Calculated: C 68.80 H 6.22 N 3.09 Cl 7.81
Found: 68.61 6.05 3.07 8.01 ac) 4'-[2-[N-(2-(3-Chloro-phenyl)-2-hydroxy-ethyl)amino]ethyl]-2-methoxy-diphenylmethane Prepared from 3-chloro-phenacylbromide and 4'-(2-amino-ethyl)-2-methoxy-diphenylmethane-hydrochloride with the addition of N,N-diisopropyl-ethylamine.

Melting point: 73°–75° C.
Calculated: C 72.80 H 6.62 N 3.54
Found: 72.53 6.61 3.44

Example 3

Ethyl 4'-[2-[N-(2-hydroxy-2-phenyl-ethyl)amino]ethyl]biphenylyl-4-carboxylate 1.0 g (3.27 mmol) of ethyl 4'-(2-amino-ethyl)biphenylyl-4-carboxylate hydrochloride are combined with 367 mg (3.27 mmol) of potassium tert.butoxide in 10 ml of absolute ethanol and heated to reflux temperature under nitrogen. After 5 minutes, 0.37 ml (3.27 mmol) of styrene oxide dissolved in 10 ml of absolute ethanol are added dropwise. The mixture is then refluxed for a further 3 hours. After cooling, it is concentrated by evaporation and purified by column chromatography on silica gel using chloroform/methanol=15:1 as eluant. Finally it is recrystallised from acetonitrile.

Yield: 270 mg (21.3% of theory),
Melting point: 116°–117° C.
Calculated: C 77.09 H 6.99 N 3.60
Found 77.10 6.92 3.57

Analogously to Example 3 the following compounds are prepared:

a) 4'-Hydroxy-4-[2-[N-(2-hydroxy-2-phenyl-ethyl)amino]ethyl]biphenyl Prepared from styrene oxide and 4'-(2-amino-ethyl)-4-hydroxy-biphenyl.

Yield: 14.2% of theory,
Melting point: 134°–136° C.
Calculated: C 79.25 H 6.95 N 4.20
Found: 79.10 7.06 4.24 b) 4-[2-[N-(2-Hydroxy-2-phenyl-ethyl)amino]propyl]biphenyl Prepared from styrene oxide and 4-(2-amino-propyl)biphenyl.

Yield: 27% of theory,
Melting point: 96°–100° C.
Calculated: C 83.34 H 7.60 N 4.23
Found 83.30 7.52 4.22

According to ¹H-NMR (400 MHz) there is a 1:6 mixture of pairs of diastereoisomers.

[CDCl₃: delta=4.61 ppm (dd, 0.85 H), delta=4.67 ppm (dd, 0.15 H)]

c) 4-[2-[N-(2-Hydroxy-2-phenyl-ethyl)amino]ethyl]-benzophenone-hydrochloride Prepared from styrene oxide and 4-(2-amino-ethyl)benzophenone-hydrochloride.

Yield: 17% of theory,
Melting point: 169°–172° C.
Calculated: C 72.34 H 6.33 N 3.67 Cl 9.28
Found: 72.50 6.13 3.78 9.57

Example 4

4'-[2-[N-(2-Hydroxy-2-phenyl-ethyl)amino]ethyl]-4-methoxy-diphenylmethane 2.82 g (11 mmol) of 4-[4-methoxy-benzyl]phenylacetic acid are dissolved in 25 ml of chloroform and after the addition of 2.5 ml of thionylchloride the mixture is stirred for 30 minutes at 50° C. It is then concentrated by evaporation, taken up in 30 ml of chloroform and added dropwise, with cooling, to a solution of 1.37 g (10 mmol) of 2-hydroxy-2-phenyl-ethylamine and 2.1 ml (15 mmol) of triethylamine in 40 ml of chloroform. After 2 hours stirring at ambient temperature, the mixture is washed first with dilute sodium hydroxide solution then with dilute hydrochloric acid. The chloroform extracts are then dried and concentrated by evaporation. The evaporation residue consisting of N-(2-hydroxy-2-phenyl-ethyl)-4-(4-methoxy-benzyl)phenylacetamide is dissolved in 20 ml of tetrahydrofuran and added dropwise, under nitrogen, to 1.33 g (35 mmol) of lithium aluminium hydride in 20 ml of tetrahydrofuran. After 4 hours' refluxing, 2N sodium hydroxide solution is added, the sodium aluminate formed is separated off by suction filtering and the filtrate is evaporated down. The evaporation residue is recrystallised from acetonitrile.

Yield: 890 mg (27% of theory),
Melting point: 103°–104° C.
Calculated: C 79.74 H 7.53 N 3.87
Found: 80.03 7.34 3.86

Example 5

4-[2-[N-(2-Hydroxy-2-(3-trifluoromethyl-phenyl)ethyl)amino]propyl]diphenylmethane 3.8 g (20 mmol) of 3-trifluoromethyl-acetophenone are dissolved in 70 ml of dioxan and 3 ml of water and after the addition of 2 g of kieselguhr and 2.45 g (22 mmol) of selenium dioxide, the mixture is refluxed for 6 hours. It is then cooled and filtered and 4.5 g (20 mmol) of 4-(2-amino-propyl)diphenylmethane and 2.6 g (20 mmol) of N,N-diisopropylethylamine are added to the filtrate which contains the corresponding glyoxal. After 1 hours' stirring at 35° C. the mixture is cooled in an ice bath, 50 ml of ethanol are added and, to reduce the Schiff base obtained, 1 g (26.3 mmol) of sodium borohydride is added. After 5 hours' stirring at ambient temperature the mixture is concentrated by evaporation and the evaporation residue is stirred for 15 minutes with dilute hydrochloric acid. It is then made alkaline and extracted with chloroform. The chloroform extract is evaporated down and the evaporation residue is purified by silica gel chromatography (eluant: chloroform/ethyl acetate/methanol=7/2/1).

Yield: 900 mg (11% of theory),
Melting point: 104°–107° C.
Calculated: C 72.62 H 6.34 N 3.39
Found: 72.74 6.49 3.38

According to ¹H-NMR (400 MHz) there is a 7:1 mixture of pairs of diastereoisomers.

[CDCl₃: delta=4.64 ppm (dd, 0.87 H), delta=4.57 ppm (dd, 0.13 H)]

Analogously to Example 5 the following compound is prepared:

a) 4'-[2-[N-(2-Hydroxy-2-(3-trifluoromethyl-phenyl)ethyl)amino]propyl]biphenyl-hydrochloride Prepared from 3-trifluoromethyl-acetophenone and 4-(2-aminopropyl)biphenyl.

Yield: 11% of theory,
Melting point: 188°-192° C.
Calculated: C 66.12 H 5.78 N 3.21 Cl 8.13
Found 65.98 5.66 3.10 8.22

According to ¹H-NMR (400 MHz) there is a 1:5 mixture of pairs of diastereoisomers.

[CDCl₃: delta=1.32 ppm (dd, 2.5 H), delta=1.38 ppm (dd, 0.5 H)]

Example 6

4'-[2-[N-(2-(3-Chloro-phenyl)-2-hydroxy-ethyl)amino]propyl]biphenylyl-4-carboxylic acid 0.5 g (1.1 mmol) of ethyl 4'-[2-[N-(2-(3-chloro-phenyl)-2-hydroxy-ethyl)amino]propyl]biphenylyl-4-carboxylate are suspended in 30 ml of ethanol and after the addition of 2 ml of 2N sodium hydroxide solution the mixture is stirred for 5 hours at 50° C. It is then neutralised with 4 ml of 1N hydrochloric acid, filtered and the filtrate is diluted with 40 ml of water. After standing overnight, the crystals formed are suction filtered and washed with ethanol/water=1:1.

Yield: 360 mg (80% of theory),
Melting point: 199°-201° C.
Calculated: C 70.32 H 5.90 N 3.42 Cl 8.65
Found: 70.22 5.97 3.38 8.60

According to ¹H-NMR (400 MHz) there is a 1:1 mixture of pairs of diastereoisomers.

[DMSO-d₆/CD₃OD: delta=4.98 ppm (dd), delta=5.01 ppm (dd)]

Analogously to Example 6 the following compound is prepared:

4'-[2-[N-(2-(3-chloro-phenyl)-2-hydroxy ethyl)amino]propyl]biphenylyl-4-oxyacetic acid Prepared from ethyl 4'-[2-[N-(2-(3-chloro-phenyl)-2-hydroxy-ethyl)-amino]propyl]biphenylyl-4-oxyacetate Yield: 95.5% of theory,
Melting point: 216°-218° C.
Calculated: C 68.25 H 5.96 N 3.18
Found: 68.37 5.97 3.26

According to ¹H-NMR (400 MHz) there is a 1:1 mixture of pairs of diastereoisomers.

Example 7

Ethyl 4'-[2-[N-(2-(3-chloro-phenyl)-2-hydroxy-ethyl)amino]ethyl]biphenylyl-4-carboxylate 1.7 g (10 mmol) of 2-(3-chloro-phenyl)-2-hydroxyethylamine and 3.66 g (11 mmol) of ethyl 4'-(2-bromoethyl)biphenylyl-4-carboxylate are dissolved in 50 ml of dimethylformamide and after the addition of 2.8 g (20 mmol) of potassium carbonate the mixture is stirred for 3 hours at 90° to 100° C. It is then filtered, concentrated by evaporation and the evaporation residue is purified by column chromatography on silica gel (eluant: ethyl acetate/methanol=40:1).

Yield: 1.52 g (36% of theory),
Melting point: 120°-122° C.
Calculated: C 70.83 H 6.18 N 3.30 Cl 8.36
Found: 70.76 6.09 3.24 8.46

Analogously to Example 7 the following compound is prepared:

a) 4-[2-[N-(2-(3-Chloro-phenyl)-2-hydroxy-ethyl)amino]ethyl]diphenylmethane Prepared from 2-(3-chloro-phenyl)-2-hydroxy-ethylamine and 4-(2-bromoethyl)diphenylmethane.

Yield: 37% of theory,
Melting point: 85°-87° C.
Calculated: C 75.50 H 6.61 N 3.83 Cl 9.69
Found: 75.63 6.72 3.69 9.57

Example 8

4'-[2-[N-(2-(3-Chloro-phenyl)-2-hydroxy-ethyl)amino]propyl]-4-(2-hydroxy-ethoxy)biphenyl A solution of 1.75 g (3.85 mmol) of methyl 4'-[2-[N-(2-(3-chloro-phenyl)-2-hydroxy-ethyl)amino]propyl]-biphenylyl-4-oxyacetate in 30 ml of absolute tetrahydrofuran is added dropwise, with stirring, to 1.75 g (46 mmol) of lithium aluminium hydride in 40 ml of absolute tetrahydrofuran. The mixture is then refluxed for 1 hour, decomposed by the dropwise addition of 4N sodium hydroxide solution and filtered to remove the sodium aluminate formed. The filtrate is evaporated down and the residue is recrystallised from acetonitrile.

Yield: 660 mg (40.2% of theory),
Melting point: 120°-126° C.
Calculated: C 70.49 H 6.63 N 3.29
Found: 70.50 6.76 3.42

According to ¹H-NMR (400 MHz) there is a 1:1 mixture of pairs of diastereoisomers.

[CDCl₃: delta=4.56 ppm (dd, 0.5 H), delta=4.62 ppm (dd, 0.5 H)]

Example I

Coated tablet containing 10 mg of ethyl 4'-[2-[N-(2-(3-chloro-phenyl)-2-hydroxy-ethyl)amino]propyl]diphenylmethane-2-carboxylate

| Composition 1 coated tablet contains: | |
| --- | --- |
| (1) Active substance | 10.0 mg |
| (2) Lactose | 69.0 mg |
| (3) Corn starch | 35.0 mg |
| (4) Polyvinylpyrrolidone | 5.0 mg |
| (5) Magnesium stearate | 1.0 mg |
| | 120.0 mg |

Preparation (1)+(2)+(3) are mixed together and moistened with (4) in an aqueous solution. The moist mass is passed through a screen with a mesh size of 1.6 mm and dried at 45° C. in a circulating air dryer. The dry granules are passed through a screen with a mesh size of 1 mm and mixed with (5). The finished mixture is compressed to make tablet cores.

| Weight of core: | 120.0 mg |
| --- | --- |
| Diameter: | 7.0 mm |
| Radius of curvature: | 6.0 mm |

The tablet cores thus produced are coated in known manner with a coating consisting essentially of sugar

Example II

Coated tablet containing 50 mg of ethyl 4'-[2-[N-(2-(3-chloro-phenyl)-2-hydroxy-ethyl)amino]-propyl]diphenylmethane-2-carboxylate

| Composition 1 coated tablet contains: | |
|---|---|
| (1) Active substance | 50.0 mg |
| (2) Lactose | 110.8 mg |
| (3) Corn starch | 50.0 mg |
| (4) Polyvinylpyrrolidone | 8.0 mg |
| (5) Magnesium stearate | 1.2 mg |
| | 220.0 mg |

Preparation

The coated tablets are prepared analogously to Example 1.
Weight of core: 220.0 mg
Diameter: 9.0 mm
Radius of curvature: 8.0 mm
Weight of coated tablet: 300.0 mg

Example III

Tablets containing 150 mg of ethyl 4'-[2-[N-(2-(3-chloro-phenyl)-2-hydroxy-ethyl)amino]-propyl]diphenylmethane-2-carboxylate

| Composition 1 tablet contains: | |
|---|---|
| (1) Active substance | 150.0 mg |
| (2) Lactose | 86.0 mg |
| (3) Corn starch | 50.8 mg |
| (4) Microcrystalline cellulose | 25.0 mg |
| (5) Polyvinylpyrrolidone | 7.0 mg |
| (5) Magnesium stearate | 1.2 mg |
| | 320.0 mg |

Preparation (1)+(2)+(3)+(4)+(5) are mixed together and moistened with water. The moist mass is passed through a screen with a mesh size of 1.6 mm and dried at 45° C. The dry granules are passed through the same screen once more and mixed with (6). Tablets are compressed from the finished mixture.
Weight of tablet: 320.0 mg
Diameter: 10.0 mm The tablets are provided with a dividing notch to make it easier to break them in half.

Example IV

Hard gelatine capsules containing 100 mg of ethyl 4'-[2-[N-(2-(3-chloro-phenyl)-2-hydroxy-ethyl)amino]-propyl]-diphenylmethane-2-carboxylate Composition
1 capsule contains:
Capsule shell: hard gelatine capsule size 3

| Capsule contents: | |
|---|---|
| (1) Active substance | 100.0 mg |
| (2) Lactose × 1H$_2$O | 38.0 mg |
| (3) Dried corn starch | 60.0 mg |
| (4) Magnesium stearate | 2.0 mg |
| Weight of capsule filling: | 200.0 mg |
| (5) Distilled water | q.s. |

Preparation

A small amount of lactose is dissolved at about 10% in distilled water (granulating liquid). The active substance, the remaining lactose and corn starch are mixed in and moistened with the granulating liquid. The mass is screened, dried and after being screened once more, homogeneously mixed with magnesium stearate. The fine-grained granules are packed into capsules in a suitable machine.

Example V

Hard gelatine capsules containing 200 mg of ethyl 4'-[2-[N-(2-(3-chloro-phenyl)-2-hydroxy-ethyl)amino-propyl]-diphenylmethane-2-carboxylate Composition Capsule shell: hard gelatine capsules size 1

| Capsule contents: | |
|---|---|
| (1) Active substance | 200.0 mg |
| (2) Lactose × 1H$_2$O | 47.0 mg |
| (3) Dried corn starch | 70.0 mg |
| (4) Magnesium stearate | 3.0 mg |
| Weight of capsule filling: | 320.0 mg |
| (5) Distilled water | q.s. |

Preparation

A small amount of lactose is dissolved at about 10% in distilled water (granulating liquid). The active substance, the remaining lactose and corn starch are mixed in and moistened with the granulating liquid. The mass is screened, dried and after being screened once more, homogeneously mixed with magnesium stearate. The fine-grained granules are packed into capsules in a suitable machine.

Example VI

| Complete feed II for fattening pigs | |
|---|---|
| Barley | 370 g/kg |
| Wheat bran | 200 g/kg |
| Manioc flour | 135 g/kg |
| Broad beans | 100 g/kg |
| Rape extract groats | 100 g/kg |
| Edible fat | 65 g/kg |
| Lysine-rich mineral feed for pigs | 20 g/kg |
| Active substance premix | 10 g/kg |

These components in the quantities specified produce 1 kg of feed when carefully mixed together.

The 10 g of active substance premix contain, for example, 10 mg of active substance and 9.99 g of corn starch.

Example VII

| Fattening feed II for broilers | |
|---|---|
| Maize | 625 g/kg |

(page continues - "and talc. This coating may also contain colourings. The finished coated tablets are polished with wax. Weight of coated tablet: 180.0 mg")

-continued

| Fattening feed II for broilers | |
| --- | --- |
| Soya bean flour | 260 g/kg |
| Meat meal | 40 g/kg |
| Edible fat | 25 g/kg |
| Soya oil | 17 g/kg |
| Bicalcium phosphate | 12 g/kg |
| Calcium carbonate | 6 g/kg |
| Vitamin/mineral mixture | 5 g/kg |
| Active substance premix | 10 g/kg |

These components in the quantities specified produce 1 kg of feed when carefully mixed together.

The 10 g of active substance premix contain, for example, 10 mg of active substance and 9.99 g of corn starch.

Example VIII

| Feed concentrate for cattle | |
| --- | --- |
| Shredded sugar beet | 600.0 g/kg |
| Maize gluten | 100.0 g/kg |
| Malt germs | 50.0 g/kg |
| Soya bean flour | 35.0 g/kg |
| Wheat | 110.0 g/kg |
| Molasses | 60.0 g/kg |
| Edible phosphates | 12.0 g/kg |
| Calcium carbonate | 2.5 g/kg |
| Salt | 5.0 g/kg |
| Minerals | 10.0 g/kg |
| Vitamin premix | 5.5 g/kg |
| Active substance premix | 10.0 g/kg |

These components in the quantities specified produce 1 kg of feed when carefully mixed together.

The 10 g of active substance premix contain, for example, 10 mg of active substance and 9.99 g of corn starch.

Example IX

| Fattening feed for lambs | |
| --- | --- |
| Barley | 690 g/kg |
| Soya bean flour | 100 g/kg |
| Maize | 150 g/kg |
| Molasses | 30 g/kg |
| Vitamin/mineral mixture | 20 g/kg |
| Active substance premix | 10 g/kg |

These components in the quantities specified produce 1 kg of feed when carefully mixed together.

The 10 g of active substance premix contain, for example, 10 mg of active substance and 9.99 g of corn starch.

We claim:

1. A method for accelerating weight gain and reducing fatty deposits in an animal which comprises administering to such animal a weight gain promoting amount of a compound of the formula

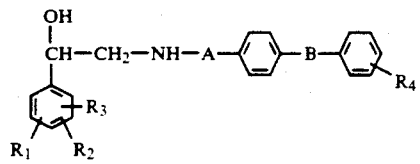

(I)

wherein

A represents a straight-chained or branched alkylene group with 1 to 5 carbon atoms, B represents a bond, an alkylene group with 1 or 2 carbon atoms, a carbonyl or hydroxymethylene group, $R_1$ represents a hydrogen atom, a halogen atom or a trifluoromethyl group, $R_2$ represents a hydrogen atom or an amino group, $R_3$ represents a cyano group, a hydrogen, chlorine or bromine atom, and $R_4$ represents a hydrogen or halogen atom, an alkyl, hydroxy, alkoxy, carboxy, alkoxycarbonyl, aminocarbonyl, alkylaminocarbonyl or dialkylaminocarbonyl group, an alkoxy group with 1 to 3 carbon atoms substituted in the end postion by a carboxy, alkoxycarbonyl, aminocarbonyl, alkylaminocarbonyl or dialkylaminocarbonyl group, or an alkoxy group with 2 or 3 carbon atoms substituted in the end position by a hydroxy, alkoxy, amino, alkylamino, dialkylamino, pyrrolidino, piperidino or hexamethyleneimino group, whilst all of the above-mentioned alkyl or alkoxy groups contain from 1 to 3 carbon atoms, unless otherwise stated, or a physiologically acceptable acid addition salt thereof.

2. The method of claim 1, wherein in the compound of formula I:

A represents an ethylene group optionally substituted by an alkyl group with 1 to 3 carbon atoms or by two methyl groups, B represents a bond, a methylene, ethylene, hydroxymethylene or carbonyl group, $R_1$ represents a hydrogen, fluorine, chlorine or bromine atom or a trifluoromethyl group, $R_2$ represents a hydrogen atom, a chlorine atom or a cyano group and $R_4$ represents a hydrogen atom, a chlorine atom, a hydroxy, methoxy, methyl, ethyl, carboxy, methoxy-carbonyl, ethoxycarbonyl, carboxymethoxy, 2-hydroxy-ethoxy, methoxycarbonylmethoxy or ethoxycarbonylmethoxy group.

3. A method for accelerating weight gain and reducing fatty deposits in an animal which comprises administering to such animal a weight gain promoting amount of a compound of the formula

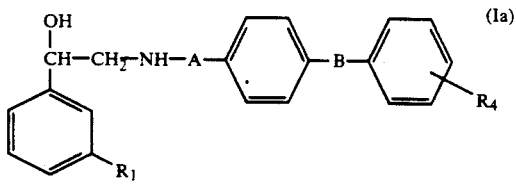

(Ia)

wherein

A represents an ethylene or methylethylene group,

B represents a bond or a methylene group, $R_1$ represents a hydrogen or chlorine atom and $R_4$ represents a hydrogen atom, a methyl, ethyl, hydroxy, methoxy, methoxycarbonyl, ethoxycarbonyl, 2-hydroxy-ethoxy, methoxycarbonylmethoxy or ethoxycarbonylmethoxy group in the 2 or 4 position, or a physiologically acceptable addition salt thereof.

4. A method for accelerating weight gain and reducing fatty deposits in an animal which comprises administering to such animal a weight gain promoting amount of 4'-[2-[N-(2(3-chloro-phenyl)-2-hydroxy-ethyl)amino]-propyl]-4-(2-hydroxy-ethoxy)biphenyl, or a physiologically acceptable acid addition salt thereof.

5. A method for accelerating weight gain and reducing fatty deposits in an animal which comprises administering to such animal a weight gain promoting amount of ethyl 4'-[2-[N-(2-(3-chloro-phenyl)-2-hydroxy-ethyl)amino]propyl]diphenylmethane-2-carboxylate, or a physiologically acceptable acid addition salt thereof.

* * * * *